United States Patent
Nakamura et al.

(10) Patent No.: US 8,304,643 B2
(45) Date of Patent: Nov. 6, 2012

(54) PHOTOELECTRIC CONVERSION MATERIAL CONTAINING FULLERENE DERIVATIVE

(75) Inventors: Eiichi Nakamura, Tokyo (JP); Yutaka Matsuo, Tokyo (JP); Katsuhiko Kanaizuka, Yamagata (JP)

(73) Assignee: Japan Science and Technology Agency, Saitama (JP)

( * ) Notice: Subject to any disclaimer, the term of this patent is extended or adjusted under 35 U.S.C. 154(b) by 801 days.

(21) Appl. No.: 12/299,894

(22) PCT Filed: May 2, 2007

(86) PCT No.: PCT/JP2007/059811
§ 371 (c)(1),
(2), (4) Date: Nov. 6, 2008

(87) PCT Pub. No.: WO2007/129768
PCT Pub. Date: Nov. 15, 2007

(65) Prior Publication Data
US 2009/0101200 A1    Apr. 23, 2009

(30) Foreign Application Priority Data
May 9, 2006 (JP) ................................. 2006-129857

(51) Int. Cl.
H01L 25/00 (2006.01)
H01L 31/00 (2006.01)
C07F 15/00 (2006.01)
C07F 17/02 (2006.01)

(52) U.S. Cl. ......... 136/243; 136/252; 556/136; 556/143
(58) Field of Classification Search ................... 136/243, 136/252; 556/136, 143
See application file for complete search history.

(56) References Cited

U.S. PATENT DOCUMENTS
2006/0234505 A1 * 10/2006 Asano et al. .................. 438/688

FOREIGN PATENT DOCUMENTS
| JP | 2002-094146 | 3/2002 |
| JP | 2003-031832 | 1/2003 |
| JP | 2003-238692 | 8/2003 |
| JP | 2005-236278 | 9/2005 |

OTHER PUBLICATIONS

Toganoh et al. "Synthesis of Ferrocene/Hydr0Niierene Hybrid and Functionaiized BuckFerrocenes", J. Am.Chem. Soc., 125 (46), 13974-13975 (2003).*

Matsuo, Y., et al.: "Remote Chirality Transfer within a Coordination Sphere by the Use of a Ligand Possessing a Concave Cavity", Organometallics, vol. 25, pp. 2826-2832, 2006.

Matsuo, Y., et al.: "Synthesis and Derivatization fo Iridium(I) and Iridium(III) Pentamethlyl[60]fullerene Complexes", Organometallics, vol. 24, pp. 89-85, 2005.

Toganoh, M., et al.: "Synthesis of Ferrocene/Hydrofullerene Hybrid and Functionalized Buck Ferrocenes", J. Am. Chem. Soc., vol. 125, pp. 13974-13975, 2003.

* cited by examiner

*Primary Examiner* — Ling Choi
*Assistant Examiner* — Monique Peets
(74) *Attorney, Agent, or Firm* — Morgan, Lewis & Bockius LLP

(57) ABSTRACT

The present invention provides a photoelectric conversion material comprising a fullerene derivative represented by the formula $C_{60}(R^1)_5(ML_n)$, wherein: each $R^1$ independently represents an organic group having a substituent; M represents a metal atom; L is a ligand of M; and n is the number of Ls. Further, the present invention also provides a photoelectric conversion device having a self-assembled monomolecular film of the photoelectric conversion material, and a solar cell having the photoelectric conversion device.

13 Claims, 2 Drawing Sheets methyl viologen methyl viologen methyl viologen

PHOTOELECTRIC CONVERSION MATERIAL CONTAINING FULLERENE DERIVATIVE

CROSS REFERENCE TO RELATED APPLICATIONS

This application is a U.S. National Phase Application of International Application Number PCT/JP2007/059811, filed May 2, 2007, which claims the benefit of Japanese Patent Application No. 2006-129857, filed May 9, 2006, each of which is incorporated by reference in its entirety.

TECHNICAL FIELD

The present invention relates to a photoelectric conversion material comprising a fullerene derivative, a photoelectric conversion device having a self-assembled monomolecular film of the photoelectric conversion material, and a solar cell having the photoelectric conversion device.

BACKGROUND ART

Since the method for synthesizing a carbon cluster (hereinafter also referred to as "fullerene"), in which carbon atoms are arranged to form a spherical shape or a rugby ball shape, was established, fullerene has been energetically studied. As a result, many fullerene derivatives have been synthesized.

In general, fullerene derivatives have a widely-extended π electron system. Further, characteristically, fullerene derivatives have a relatively small HOMO-LUMO gap (about 1.5-2.0 eV), and also have optical absorption property in a wide wavelength range and highly-efficient light-emitting property via Singlet-to-Triplet intersystem crossing. Further, fullerenes are constituted only by carbon atoms, and at the same time, exhibit multistep reversible redox reaction (6-electron reduction). Attributed to these properties, there are wide range of possibilities for application of fullerene derivatives. For example, it is thought that fullerene derivatives can be utilized for FET, organic EL, solar cells, catalysts, etc.

Regarding a photoelectric conversion device utilizing optical absorption property of fullerene metal complexes, studies of the development of artificial photosynthesis utilizing high electron acceptor ability of fullerenes have been reported. Specifically, there are the following reports: a wet solar cell comprising a monomolecular film prepared by molecules, which are joined via chemical bond using ferrocene (electron donor)-porphyrin (optical absorption center)-fullerene (electron acceptor) on a gold electrode [Eur. J. Org. Chem. 2445. (1999) (non-patent document 1)]; and a wet solar cell, wherein molecules in which fullerene metal complex and porphyrin are joined together are immobilized on an ITO electrode [J. Am. Chem. Soc. 127, 2380, (2005) (non-patent document 2)].

However, regarding such solar cells, synthesis of fullerene derivatives to be used in photoelectric conversion devices thereof is complicated. In addition, there is a problem that desired properties cannot be sufficiently exerted.

DISCLOSURE OF THE INVENTION

Under the above-described circumstances, for example, fullerene derivatives having very high quantum yield of photocurrent generation are desired. Moreover, fullerene derivatives, which have very high quantum yield of photocurrent generation, and which can be easily synthesized, are desired. In addition, solar cells having high power generation efficiency are desired.

The present inventors found fullerene derivatives having high quantum yield of photocurrent generation among fullerene derivatives which can be relatively easily synthesized, and completed the present invention based on this finding. The present invention provides a photoelectric conversion material comprising a fullerene derivative as described below, a photoelectric conversion device having a self-assembled monomolecular film of the photoelectric conversion material, and a solar cell having the photoelectric conversion device.

[1] A photoelectric conversion material comprising a fullerene derivative represented by the following formula (1):

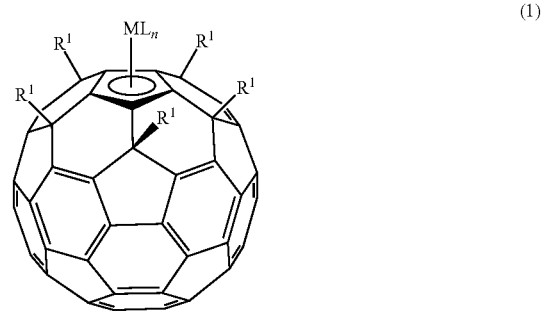

wherein: each $R^1$ independently represents an organic group having a substituent; M represents a metal atom; L is a ligand of M; and n is the number of Ls.

In item [1], it is preferred that each $R^1$ is independently an organic group comprising a carboxylic acid group. Further, M is preferably Fe or Ru.

[2] A photoelectric conversion device having a self-assembled monomolecular film of the photoelectric conversion material according to item [1].

[3] A solar cell having the photoelectric conversion device according to item [2].

[4] A photoelectric conversion material comprising a fullerene derivative represented by the following formula (10):

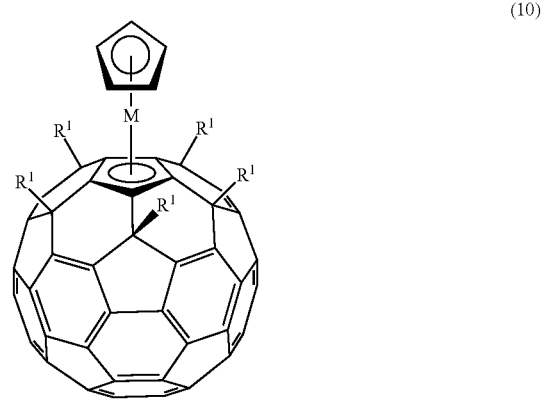

wherein: each $R^1$ independently represents a $C_1$-$C_{30}$ hydrocarbon group, a $C_1$-$C_{30}$ alkoxy group, a $C_6$-$C_{30}$ aryloxy group, an amino group, a silyl group, an alkylthio group ($-SY^1$: in the formula, $Y^1$ represents a substituted or unsubstituted $C_1$-$C_{30}$ alkyl group), an arylthio group ($-SY^2$: in the formula, $Y^2$ represents a substituted or unsubstituted $C_6$-$C_{18}$ aryl group), an alkylsulfonyl group ($-SO_2Y^3$: in the formula, $Y^3$ represents a substituted or unsubstituted $C_1$-$C_{30}$ alkyl group), or an arylsulfonyl group ($-SO_2Y^4$: in the formula, $Y^4$ represents a substituted or unsubstituted $C_6$-$C_{18}$ aryl group), which has a carboxylic acid group, a phosphate group, a phosphonate group or $-SiO_3$; and M represents a metal atom.

[5] The photoelectric conversion material according to item [4], wherein each $R^1$ independently represents a $C_1$-$C_{30}$ alkyl group, a $C_2$-$C_{30}$ alkenyl group, a $C_2$-$C_{30}$ alkynyl group, a $C_4$-$C_{30}$ alkyldienyl group, a $C_6$-$C_{18}$ aryl group, a $C_7$-$C_{30}$ alkylaryl group, a $C_7$-$C_{30}$ arylalkyl group, a $C_4$-$C_{30}$ cycloalkyl group or a $C_4$-$C_{30}$ cycloalkenyl group, which has a carboxylic acid group, a phosphate group, a phosphonate group or $-SiO_3$.

In item [5], it is preferred that each $R^1$ is independently an organic group comprising a carboxylic acid group. Further, M is preferably Fe or Ru.

[6] A photoelectric conversion material comprising a fullerene derivative represented by the following formula (11):

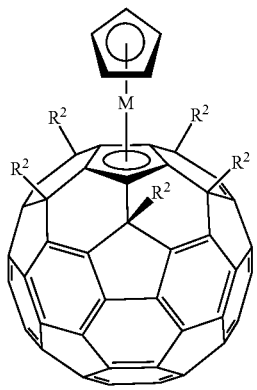

(11)

wherein:
each $R^2$ is independently a group represented by the following formula (A):

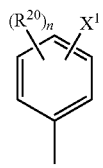

(A)

wherein: $X^1$ represents a carboxylic acid group, a phosphate group, a phosphonate group or $-SiO_3$; M represents a metal atom; each $R^{20}$ independently represents an organic group; and n is an integer from 0 to 4; and M represents a metal atom.

In item [6]: it is preferred that each $X^1$ independently represents a carboxylic acid group; n is preferably 0; and $X^1$ is preferably at the para position.

[7] A photoelectric conversion material comprising a fullerene derivative represented by the following formula (12):

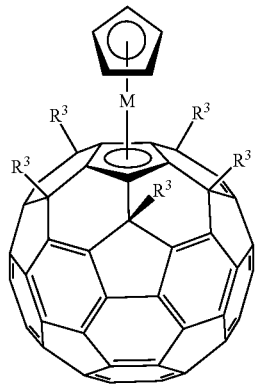

(12)

wherein:
each $R^3$ is independently a group represented by the following formula (B):

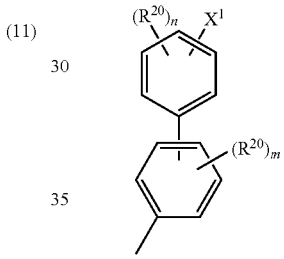

(B)

wherein: $X^1$ represents a carboxylic acid group, a phosphate group, a phosphonate group or $-SiO_3$; M represents a metal atom; each $R^{20}$ independently represents an organic group; n is an integer from 0 to 4; and m is an integer from 0 to 4; and M represents a metal atom.

In item [7], the group represented by the formula (B) is preferably a group represented by the following formula (B 1):

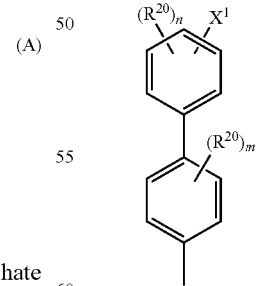

(B1)

wherein: $X^1$ represents a carboxylic acid group, a phosphate group, a phosphonate group or $-SiO_3$; M represents a metal atom; each $R^{20}$ independently represents an organic group; n is an integer from 0 to 4; and m is an integer from 0 to 4.

In the formula (B) or (B1): it is preferred that each $X^1$ independently represents a carboxylic acid group; it is preferred that n and m are each independently 0; and $X^1$ is preferably at the para position.

[8] The photoelectric conversion material according to any one of items [4] to [7], wherein M represents Fe or Ru.

[9] A photoelectric conversion device having a self-assembled monomolecular film of the photoelectric conversion material according to any one of items [4] to [8].

[10] A photoelectric conversion device having an ITO electrode on which the self-assembled monomolecular film of the photoelectric conversion material according to any one of items [4] to [8] is formed.

[11] A solar cell having the photoelectric conversion device according to item [9] or [10].

[12] A photoelectric conversion material comprising a fullerene derivative represented by the following formula (10):

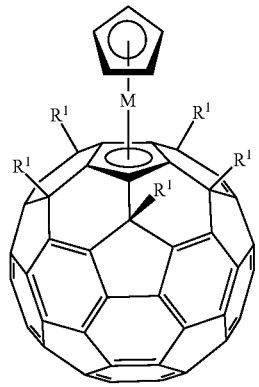

(10)

wherein: each $R^1$ independently represents a $C_1$-$C_{30}$ hydrocarbon group, a $C_1$-$C_{30}$ alkoxy group, a $C_6$-$C_{30}$ aryloxy group, an amino group, a silyl group, an alkylthio group (—$SY^1$: in the formula, $Y^1$ represents a substituted or unsubstituted $C_1$-$C_{30}$ alkyl group), an arylthio group (—$SY^2$: in the formula, $Y^2$ represents a substituted or unsubstituted $C_6$-$C_{18}$ aryl group), an alkylsulfonyl group (—$SO_2Y^3$: in the formula, $Y^3$ represents a substituted or unsubstituted $C_1$-$C_{30}$ alkyl group), or an arylsulfonyl group (—$SO_2Y^4$: in the formula, $Y^4$ represents a substituted or unsubstituted $C_6$-$C_{18}$ aryl group), which has a thiol group or a disulfide group; and M represents a metal atom.

[13] The photoelectric conversion material according to item [12], wherein each $R^1$ independently represents a $C_1$-$C_{30}$ alkyl group, a $C_2$-$C_{30}$ alkenyl group, a $C_2$-$C_{30}$ alkynyl group, a $C_4$-$C_{30}$ alkyldienyl group, a $C_6$-$C_{18}$ aryl group, a $C_7$-$C_{30}$ alkylaryl group, a $C_7$-$C_{30}$ arylalkyl group, a $C_4$-$C_{30}$ cycloalkyl group or a $C_4$-$C_{30}$ cycloalkenyl group, which has a thiol group or a disulfide group.

[14] A photoelectric conversion device having a self-assembled monomolecular film of the photoelectric conversion material according to item [12] or [13].

[15] A photoelectric conversion device having a gold electrode on which the self-assembled monomolecular film of the photoelectric conversion material according to item [12] or [13] is formed.

[16] A solar cell having the photoelectric conversion device according to item [14] or [15].

When using the fullerene derivative according to the preferred embodiment of the present invention, for example, a photoelectric conversion material having very high quantum yield of photocurrent generation can be provided. Moreover, for example, a photoelectric conversion material having very high quantum yield of photocurrent generation, which comprises a fullerene derivative that can be easily synthesized, can be provided. The photoelectric conversion device according to the preferred embodiment of the present invention has high quantum yield. Furthermore, the solar cell according to the preferred embodiment of the present invention can efficiently generate electric power, and it can be produced at a lower cost.

BEST MODE FOR CARRYING OUT THE INVENTION

Figure 1:
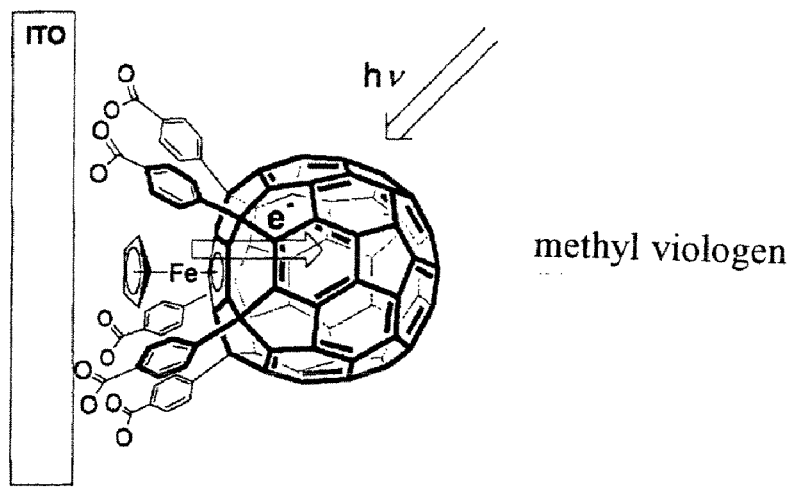
FIG. 1 shows a mechanism of photoelectric conversion using a photoelectric conversion device.
Figure 1:
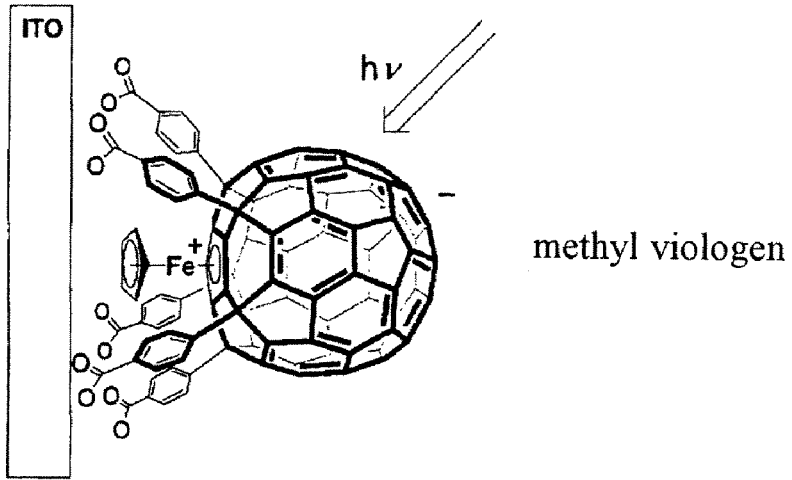
Figure 1:
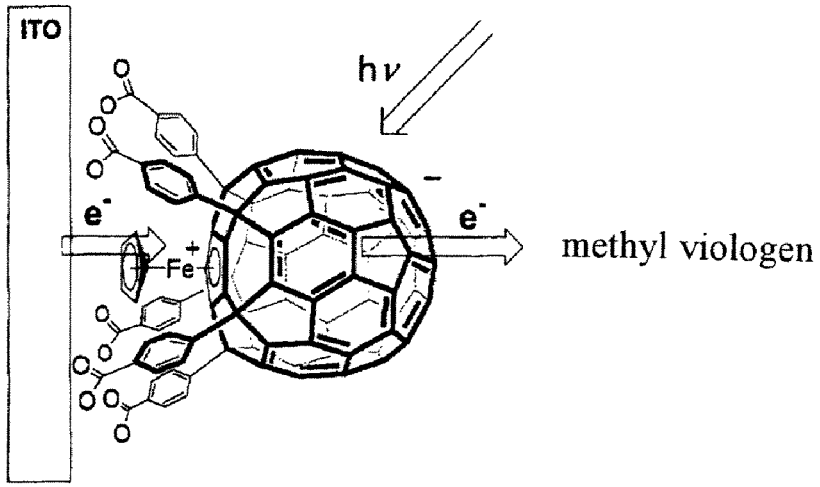

1. Fullerene Derivative Included in the Photoelectric Conversion Material of the Present Invention As described above, the fullerene derivative obtained using the production method of the present invention is a fullerene derivative represented by the formula $C_{60}(R^1)_5(MLn)$, wherein: each $R^1$ independently represents an organic group having a substituent; M represents a metal atom; L is a ligand of M; and n is the number of Ls. Specifically, it is a fullerene derivative represented by the above-described formula (1).

In formula (1), each $R^1$ independently represents an organic group having a substituent. Among such organic groups, it is preferred that each $R^1$ independently represents a hydrogen atom, a substituted or unsubstituted $C_1$-$C_{30}$ hydrocarbon group, a substituted or unsubstituted $C_1$-$C_{30}$ alkoxy group, a substituted or unsubstituted $C_6$-$C_{30}$ aryloxy group, a substituted or unsubstituted amino group, a substituted or unsubstituted silyl group, a substituted or unsubstituted alkylthio group (—$SY^1$: in the formula, $Y^1$ represents a substituted or unsubstituted $C_1$-$C_{30}$ alkyl group), a substituted or unsubstituted arylthio group (—$SY^2$: in the formula, $Y^2$ represents a substituted or unsubstituted $C_6$-$C_{18}$ aryl group), a substituted or unsubstituted alkylsulfonyl group (—$SO_2Y^3$: in the formula, $Y^3$ represents a substituted or unsubstituted $C_1$-$C_{30}$ alkyl group), or a substituted or unsubstituted arylsulfonyl group (—$SO_2Y^4$: in the formula, $Y^4$ represents a substituted or unsubstituted $C_6$-$C_{18}$ aryl group).

$R^1$ can have one or more substituents selected from the group consisting of a carboxylic acid group, a phosphate group, a phosphonate group, —$SiO_3$, a thiol group, a disulfide group, an ester group, an amide group, an alkyne group, a trimethylsilyl group, a trimethylsilylethynyl group, an aryl group, an amino group, a phosphonyl group, a thio group, a carbonyl group, a nitro group, a sulfo group, an imino group, a halogeno group, and an alkoxy group. Among these substituents, it is preferred that $R^1$ has one or more substituents selected from the group consisting of a carboxylic acid group, a phosphate group, a phosphonate group, —$SiO_3$, a thiol group, and a disulfide group.

In formula (1), M is not particularly limited as long as it is a metal atom, and it may be a typical metal or a transition metal. Specific examples of M include typical metals such as Li, K, Na, Mg and Al, and transition metals such as Ti, Zr, V, Cr. Mo, W, Mn, Re, Fe, Ru, Os, Rh, Ir, Ni, Pd, Pt, Cu and Zn. When a fullerene derivative obtained is used for an electronic material, M is preferably a transition metal because electronic property based on redox behavior specific to the metal is imparted to the fullerene skeleton. Moreover, among transition metals, group 8-10 transition metals such as Fe, Ru, Os, Rh, Ir, Ni, Pd and Pt are preferred. Furthermore, group 8 transition metals such as Fe, Ru and Os are more preferred, and Fe and Ru are particularly preferred.

In formula (1), n is the number of Ls (L: ligand of M), and is not particularly limited as long as it is equal to or less than an integer which can be the number of ligands of M and is 0 or more. Preferably, n is an integer from 0 to 5. When there are 2 or more Ls, such ligand Ls may be the same or different.

Further, L is preferably a hydrogen atom, a halogen atom such as Cl, Br and I, an alkoxy group such as a methoxy group and an ethoxy group, an alkyl group such as a methyl group and an ethyl group, a carbonyl group, an alkyne group, or a cyclopentadienyl group.

When a fullerene derivative represented by formula (1) is used for an ITO (indium tin oxide) electrode, in formula (1), it is preferred that each $R^1$ independently represents a $C_1$-$C_{30}$ hydrocarbon group, a $C_1$-$C_{30}$ alkoxy group, a $C_6$-$C_{30}$ aryloxy group, an amino group, a silyl group, an alkylthio group (—$SY^1$: in the formula, $Y^1$ represents a substituted or unsubstituted $C_1$-$C_{30}$ alkyl group), an arylthio group (—$SY^2$: in the formula, $Y^2$ represents a substituted or unsubstituted $C_6$-$C_{18}$ aryl group), an alkylsulfonyl group (—$SO_2Y^3$: in the formula, $Y^3$ represents a substituted or unsubstituted $C_1$-$C_{30}$ alkyl group), or an arylsulfonyl group (—$SO_2Y^4$: in the formula, $Y^4$ represents a substituted or unsubstituted $C_6$-$C_{18}$ aryl group), which has a carboxylic acid group, a phosphate group, a phosphonate group or —$SiO_3$. It is more preferred that each $R^1$ independently represents a $C_1$-$C_{30}$ alkyl group, a $C_2$-$C_{30}$ alkenyl group, a $C_2$-$C_{30}$ alkynyl group, a $C_4$-$C_{30}$ alkyldienyl group, a $C_6$-$C_{18}$ aryl group, a $C_7$-$C_{30}$ alkylaryl group, a $C_7$-$C_{30}$ arylalkyl group, a $C_4$-$C_{30}$ cycloalkyl group or a $C_4$-$C_{30}$ cycloalkenyl group, which has a carboxylic acid group, a phosphate group, a phosphonate group or —$SiO_3$. Furthermore, in formula (1), it is preferred that each $R^1$ is independently a group represented by the following formula (A):

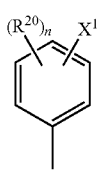

(A)

wherein: $X^1$ represents a carboxylic acid group, a phosphate group, a phosphonate group or —$SiO_3$; M represents a metal atom; each $R^{20}$ independently represents an organic group; and n is an integer from 0 to 4, or a group represented by the following formula (B):

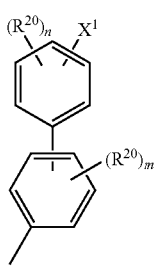

(B)

wherein: $X^1$ represents a carboxylic acid group, a phosphate group, a phosphonate group or —$SiO_3$; M represents a metal atom; each $R^{20}$ independently represents an organic group; n is an integer from 0 to 4; and m is an integer from 0 to 4. In this regard, in formulae (A) and (B), both n and m are preferably 0. Further, $R^{20}$ is not particularly limited as long as it is an organic group, but it is preferably a $C_1$-$C_{30}$ hydrocarbon group.

It is particularly preferred that the group represented by formula (A) is a group represented by the following formula:

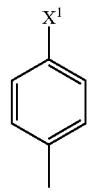

wherein each $X^1$ independently represents a carboxylic acid group, a phosphate group, a phosphonate group, —$SiO_3$, a thiol group, or a disulfide group. Further, it is particularly preferred that the group represented by formula (B) is a group represented by the following formula:

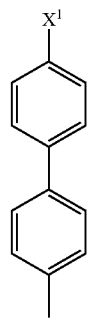

wherein each $X^1$ independently represents a carboxylic acid group, a phosphate group, a phosphonate group, —$SiO_3$, a thiol group, or a disulfide group.

In the present specification, the hydrocarbon group of the "$C_1$-$C_{30}$ hydrocarbon group" may be a saturated or unsaturated acyclic group or a saturated or unsaturated cyclic group. When the $C_1$-$C_{30}$ hydrocarbon group is acyclic, it may be linear or branched. The "$C_1$-$C_{30}$ hydrocarbon group" includes $C_1$-$C_{30}$ alkyl group, $C_2$-$C_{30}$ alkenyl group, $C_2$-$C_{30}$ alkynyl group, $C_4$-$C_{30}$ alkyldienyl group, $C_6$-$C_{18}$ aryl group, $C_7$-$C_{30}$ alkylaryl group, $C_7$-$C_{30}$ arylalkyl group, $C_4$-$C_{30}$ cycloalkyl group, $C_4$-$C_{30}$ cycloalkenyl group, and ($C_3$-$C_{10}$ cycloalkyl) $C_1$-$C_{10}$ alkyl group.

In the present specification, the "$C_1$-$C_{30}$ alkyl group" is preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, the "$C_2$-$C_{30}$ alkenyl group" is preferably $C_2$-$C_{10}$ alkenyl group, and more preferably $C_2$-$C_6$ alkenyl group. Examples of alkenyl groups include, but are not limited to, vinyl, allyl, propenyl, isopropenyl, 2-methyl-1-propenyl, 2-methylallyl, and 2-butenyl.

In the present specification, the "$C_2$-$C_{30}$ alkynyl group" is preferably $C_2$-$C_{10}$ alkynyl group, and more preferably $C_2$-$C_6$ alkynyl group. Examples of alkynyl groups include, but are not limited to, ethynyl, propynyl, and butynyl.

In the present specification, the "$C_4$-$C_{30}$ alkyldienyl group" is preferably $C_4$-$C_{10}$ alkyldienyl group, and more preferably $C_4$-$C_6$ alkyldienyl group. Examples of alkyldienyl groups include, but are not limited to, 1,3-butadienyl.

In the present specification, the "$C_6$-$C_{18}$ aryl group" is preferably $C_6$-$C_{10}$ aryl group. Examples of aryl groups include, but are not limited to, phenyl, 1-naphthyl, 2-naphthyl, indenyl, biphenylyl, anthryl, and phenanthryl.

In the present specification, the "$C_7$-$C_{30}$ alkylaryl group" is preferably $C_7$-$C_{12}$ alkylaryl group. Examples of alkylaryl groups include, but are not limited to, o-tolyl, m-tolyl, p-tolyl, 2,3-xylyl, 2,4-xylyl, 2,5-xylyl, o-cumenyl, m-cumenyl, p-cumenyl, and mesityl.

In the present specification, the "$C_7$-$C_{30}$ arylalkyl group" is preferably $C_7$-$C_{12}$ arylalkyl group. Examples of arylalkyl groups include, but are not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, and 5-phenylpentyl.

In the present specification, the "$C_4$-$C_{30}$ cycloalkyl group" is preferably $C_4$-$C_{10}$ cycloalkyl group. Examples of cycloalkyl groups include, but are not limited to, cyclopropyl, cyclobutyl, cyclopentyl, and cyclohexyl.

In the present specification, the "$C_4$-$C_{30}$ cycloalkenyl group" is preferably $C_4$-$C_{10}$ cycloalkenyl group. Examples of cycloalkenyl groups include, but are not limited to, cyclopropenyl, cyclobutenyl, cyclopentenyl, and cyclohexenyl.

In the present specification, the "$C_1$-$C_{30}$ alkoxy group" is preferably $C_1$-$C_{10}$ alkoxy group, and more preferably $C_1$-$C_6$ alkoxy group. Examples of alkoxy groups include, but are not limited to, methoxy, ethoxy, propoxy, butoxy, and pentyloxy.

In the present specification, the "$C_6$-$C_{30}$ aryloxy group" is preferably $C_6$-$C_{10}$ aryloxy group. Examples of aryloxy groups include, but are not limited to, phenyloxy, naphthyloxy, and biphenyloxy.

In the present specification, in "alkylthio group (—$SY^1$: in the formula, $Y^1$ is a substituted or unsubstituted $C_1$-$C_{30}$ alkyl group)" and "alkylsulfonyl group (—$SO_2Y^3$: in the formula, $Y^3$ is a substituted or unsubstituted $C_1$-$C_{30}$ alkyl group)", $Y^1$ and $Y^3$ are preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, in "arylthio group (—$SY^2$: in the formula, $Y^2$ is a substituted or unsubstituted $C_6$-$C_{18}$ aryl group)" and "arylsulfonyl group (—$SO_2Y^4$: in the formula, $Y^4$ is a substituted or unsubstituted $C_6$-$C_1$, aryl group)", $Y^2$ and $Y^4$ are preferably $C_6$-$C_{10}$ aryl group. Examples of aryl groups include, but are not limited to, phenyl, 1-naphthyl, 2-naphthyl, indenyl, biphenylyl, anthryl, and phenanthryl.

2. Method for Producing a Fullerene Derivative Included in the Photoelectric Conversion Material of the Present Invention The method for producing a fullerene derivative included in the photoelectric conversion material of the present invention is not particularly limited. However, for example, a fullerene derivative can be synthesized by reacting: a fullerene; a halogenated organic compound (A) represented by the following formula (2):

$$R^4 X^2 \quad (2)$$

wherein $R^4$ represents an organic group, and $X^2$ represents a halogen atom; a Grignard reagent (B) represented by the following formula (3):

$$R^5 MgX^3 \quad (3)$$

wherein $R^5$ represents an organic group, and $X^3$ represents a halogen atom; and an organocopper reagent (C) prepared from a monovalent or divalent copper compound.

2.1. Fullerene

Examples of fullerenes to be used in the method for producing the fullerene derivative of the present invention include fullerene $C_{60}$ (so-called "buckminsterfullerene").

2.2. Halogenated Organic Compound (A)

The halogenated organic compound (A) to be used in the production method of the present invention is represented by the above-described formula (2).

In formula (2), $R^4$ is not particularly limited as long as it is an organic group. However, for example, $R^4$ represents a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ represents a substituted or unsubstituted $C_1$-$C_{20}$ alkyl group), a substituted or unsubstituted arylthio group (—$SY^2$: in the formula, $Y^2$ represents a substituted or unsubstituted $C_6$-$C_{18}$ aryl group), a substituted or unsubstituted alkylsulfonyl group (—$SO_2Y^3$: in the formula, $Y^3$ represents a substituted or unsubstituted $C_1$-$C_{20}$ alkyl group), or a substituted or unsubstituted arylsulfonyl group (—$SO_2Y^4$: in the formula, $Y^4$ represents a substituted or unsubstituted $C_6$-$C_{18}$ aryl group).

More specifically, $R^4$ may have substituents comprising functional groups such as an ester group, a carboxyl group, an amide group, an alkyne group, a trimethylsilyl group, a trimethylsilylethynyl group, an aryl group, an amino group, a phosphonyl group, a thio group, a carbonyl group, a nitro group, a sulfo group, an imino group, a halogeno group, and an alkoxy group. In terms of easiness of synthesis of the halogenated organic compound, $R^4$ preferably comprises one or more functional groups selected from the group consisting of an ester group, an amide group, an alkyne group, a trimethylsilyl group and an aryl group. In this case, when 2 or more functional groups are included in $R^4$, they may be the same or different.

In formula (2), $X^2$ represents a halogen atom. Among halogen atoms, $X^2$ is preferably Cl, Br or I.

2.3. Grignard Reagent (B)

The Grignard reagent (B) to be used in the production method of the present invention is represented by the above-described formula (3).

In formula (3), $R^5$ is not particularly limited as long as it is an organic group having an inactive substituent by which the Grignard reagent can be adjusted. Examples of such substituents include an alkyl group, an alkenyl group, an alkynyl group, an aralkyl group, and an aryl group.

In formula (3), $X^3$ represents a halogen atom. Among halogen atoms, $X^3$ is preferably Cl, Br or I.

2.4. Organocopper Reagent (C)

The organocopper reagent (C) to be used in the production method of the present invention is not particularly limited as long as it is prepared from a monovalent or divalent copper compound. Among them, in terms of easiness of purification and higher purity, $CuBr.S(CH_3)_2$ is preferably used as the organocopper reagent.

Further, according to circumstances, for example, in order to stabilize the organocopper reagent and improve solubility, an additive such as N,N-dimethylimidazolidinone (DMI) and N-butylpyrrolidone (NBT) can be suitably used.

2.5. Mixing Ratio Etc.

In general, the halogenated organic compound (A), the Grignard reagent (B) and the organocopper reagent (C) are used in an amount of 5 to 50 equivalents, and preferably 10 to 20 equivalents of a fullerene.

Further, in the production method of the present invention, the mixing ratio (molar ratio) of the halogenated organic compound (A) to the Grignard reagent (B) is preferably 1:0.8 to 1:1, and the mixing ratio (molar ratio) of the Grignard reagent (B) to the organocopper reagent (C) is preferably 1:0.8 to 0.8:1.

In order to synthesize a fullerene derivative with a high purity, it is preferred that slightly excessive amounts of the halogenated organic compound and the organocopper reagent are used with respect to the Grignard reagent.

2.6. Reaction Conditions

Reaction of the fullerene, the halogenated organic compound (A), the Grignard reagent (B) and the organocopper reagent (C) in the production method of the fullerene derivative included in the photoelectric conversion material of the present invention is generally performed in an inert solvent such as toluene, tetrahydrofuran, dichlorobenzene, or a mixture thereof.

The reaction is preferably performed at a temperature in the range from −70° C. to 70° C., and more preferably in the range from −50° C. to 50° C.

Further, reaction time depends on a solvent to be used, temperature, etc. In general, the reaction is performed for about several minutes to 5 hours, and preferably for about 10 minutes to 4 hours.

Termination of synthesis reaction of the fullerene derivative included in the photoelectric conversion material of the present invention can be carried out by adding an ammonium chloride solution or the like to the reaction system.

In the fullerene derivative obtained in this way, by substituting a hydrogen atom which directly binds to the fullerene skeleton with a metal atom or a metal-containing group, a fullerene derivative having a metal complex can be synthesized. Substitution can be performed using a publicly-known method. For example, such substitution can be performed by dissolving the fullerene derivative in an organic solvent and adding an organic metal (e.g., $[CpFe(CO)_2]_2$ and $[RuCp(CH_3CN)_3][PF_6]$) thereto to cause reaction.

2.7. Isolation of Fullerene Derivative

The method for isolating the fullerene derivative from the synthesis reaction system of the fullerene derivative included in the photoelectric conversion material of the present invention is not particularly limited. For example, a reaction solution is directly passed through a silica gel column to remove by-products such as inorganic substances. According to need, isolated substances are further purified by means of HPLC, usual column chromatography, etc., to improve purity of the fullerene derivative.

2.8. Conversion of Substituent Added to Fullerene Skeleton

A substituent added to a fullerene skeleton by the above-described synthesis reaction of the fullerene derivative of the present invention can be converted.

For example, a fullerene derivative to which a carboxyl group is added can be obtained by: adding a base such as NaH and NaOH to a fullerene derivative to which an ester group is added as a substituent, which is obtained by the above-described synthesis reaction of the fullerene derivative; and replacing the ester group with a carboxyl group.

3. Photoelectric Conversion Device of the Present Invention

The photoelectric conversion device of the present invention has a structure in which a self-assembled monomolecular film of the aforementioned photoelectric conversion material is formed on a support.

As the support to be used for the photoelectric conversion device of the present invention, a conductive material such as a metal plate, and a structure in which a conductive substance is provided to a nonconductive material such as a glass plate and a plastic film can be used. Examples of materials to be used for the support include metals (e.g., platinum, gold, silver, copper, aluminium, rhodium, and indium), conductive metal oxides (e.g., indium-tin composite oxide, and tin oxide doped with fluorine), and carbon. The thickness of the support is not particularly limited, but is preferably 0.3 mm to 5 mm.

Further, it is preferred that the support is substantially transparent. The term "substantially transparent" means that the light transmission rate is 10% or more. The rate is more preferably 50% or more, and most preferably 80% or more. In order to obtain a transparent support, it is preferred that a conductive layer consisting of a conductive metal oxide is provided to the surface of a glass plate or a plastic film. When using a transparent support, light incidence is preferably from the support side.

The surface resistance of the support is preferably 50 $\Omega/cm^2$ or less, and more preferably 10 $\Omega/cm^2$ or less.

A self-assembled film means a film in which a part of organic compounds constituting the film are bound to functional groups on the surface of a substrate. The self-assembled film has very few defects and has high orderliness, i.e., crystallinity. The self-assembled film can be relatively easily produced, and therefore it is easy to form the film on the substrate.

The self-assembled monomolecular film of the present invention is characterized in that a part of fullerene derivatives constituting the film are bound to the surface of a support such as an electrode.

The method for binding fullerene derivatives to the surface of a support is not particularly limited. For example, a solution of fullerene derivatives is prepared; a surface-treated substrate is immersed in the solution; and thereby the self-assembled monomolecular film of the fullerene derivatives is formed on the surface of the support. Alternatively, the monomolecular film can be formed without surface treatment.

Examples of supports to be used to obtain a material for the photoelectric conversion device of the present invention include a conductive support which is surface-treated so that it has an electric charge that is opposite to that of the functional group of the fullerene derivative used. Preferred examples of supports include an ITO electrode in which ITO is deposited on a glass substrate, a gold electrode in which gold is deposited on a glass substrate, etc.

In order to perform a treatment to impart an anionic surface on a gold electrode, for example, the gold electrode is immersed in an ethanol solution of a compound, one terminus of which has a thiol site that binds to gold, and the other terminus of which has an anionic site, such as mercaptoethanesulfonic acid (MES). After that, the gold electrode is washed with water to remove unbound MES. When preparing a cationic surface, operation is performed as in the case of the electrode with the anionic surface, using a solution of a compound, one terminus of which has a thiol site, and the other terminus of which has a cationic site (e.g., mercaptoethylamine hydrochloride).

When using an ITO electrode as a substrate, the surface thereof can be treated so as to be anionic or cationic using the same technique as that applied to the gold electrode.

Thus, the self-assembled monomolecular film of the fullerene derivative is formed on the support by immersing the support, which is surface-treated so as to be anionic or cationic, in the aforementioned solution of the fullerene derivative, and thereafter, by washing the support to remove unbound fullerene derivative. In this way, the photoelectric conversion device having the self-assembled monomolecular film of the photoelectric conversion material can be obtained.

When the support on which the monomolecular film is formed is an ITO electrode, it is preferred that each $R^1$ in the fullerene derivative represented by the above-described formula (1) included in the monomolecular film independently has a carboxylic acid group, a phosphate group, a phosphonate group or $—SiO_3$. It is more preferred that these substituents bind to the site of fullerene skeleton via π conjugated bond.

Further, when the support on which the monomolecular film is formed is a gold electrode, it is preferred that each $R^1$ in the fullerene derivative represented by the above-described formula (1) included in the monomolecular film independently has a thiol group or a disulfide group. It is more preferred that these substituents bind to the site of fullerene skeleton via π conjugated bond.

In the photoelectric conversion device of the present invention, the monomolecular film is formed on the support. However, according to need, the device may have a multilayer structure, wherein the support is further laminated with other substances. In general, such a multilayer structure can be obtained by successively immersing the support in solutions of substances, each of which has an electric charge opposite to that of the outermost layer, according to a technique known as an alternating lamination method.

4. Solar Cell of the Present Invention

The solar cell of the present invention is not particularly limited as long as it is a solar cell comprising the above-described photoelectric conversion device. Examples thereof include a cell, wherein a charge transfer layer is formed on the monomolecular film of the photoelectric conversion device of the present invention, and an opposite electrode is further formed on the charge transfer layer.

As a charge transfer layer which the solar cell of the present invention has, a publicly-known charge transfer layer is used. For example, the charge transfer layer which the solar cell of the present invention has is constituted by a disperse material of redox electrolytes. When the disperse material is a solution, it is called a liquid electrolyte. When the disperse material is dispersed in a polymer that is a solid at ordinary temperature, it is called a solid polyelectrolyte. When the disperse material is dispersed in a gel-like material, it is called a gel electrolyte. When a liquid electrolyte is used as the charge transfer layer, a solvent thereof to be used is electrochemically inactive. Examples thereof include acetonitrile, propylene carbonate and ethylene carbonate. Examples of redox electrolytes include $I^-/I_3^-$ system, $Br^-/Br_3^-$ system and quinone/hydroquinone system. These redox electrolytes can be obtained using a publicly-known method. For example, electrolytes of the $I^-/I_3^-$ system can be obtained by mixing ammonium salt of iodine with iodine.

Further, specific examples of the charge transfer layers to be used in the present invention include a liquid electrolyte that is an aqueous solution of sodium sulfate in which methyl viologen is dissolved.

The opposite electrode which the solar cell of the present invention has is not particularly limited as long as it has conductivity, and any conductive material can be used therefor. However, the electrode preferably has catalytic ability to allow oxidation of $I_3^-$ ion, etc. and reduction reaction of other redox ions with a sufficient speed. Examples of such electrodes include a platinum electrode, an electrode in which platinization or platinum deposition is applied to the surface of a conductive material, rhodium metal, ruthenium metal, ruthenium oxide and carbon.

5. Mechanism of Photoelectric Conversion Using the Photoelectric Conversion Device of the Present Invention Mechanism of photoelectric conversion using the photoelectric conversion device of the present invention will be described below based on FIGS. 1 and 2.

Figure 2:
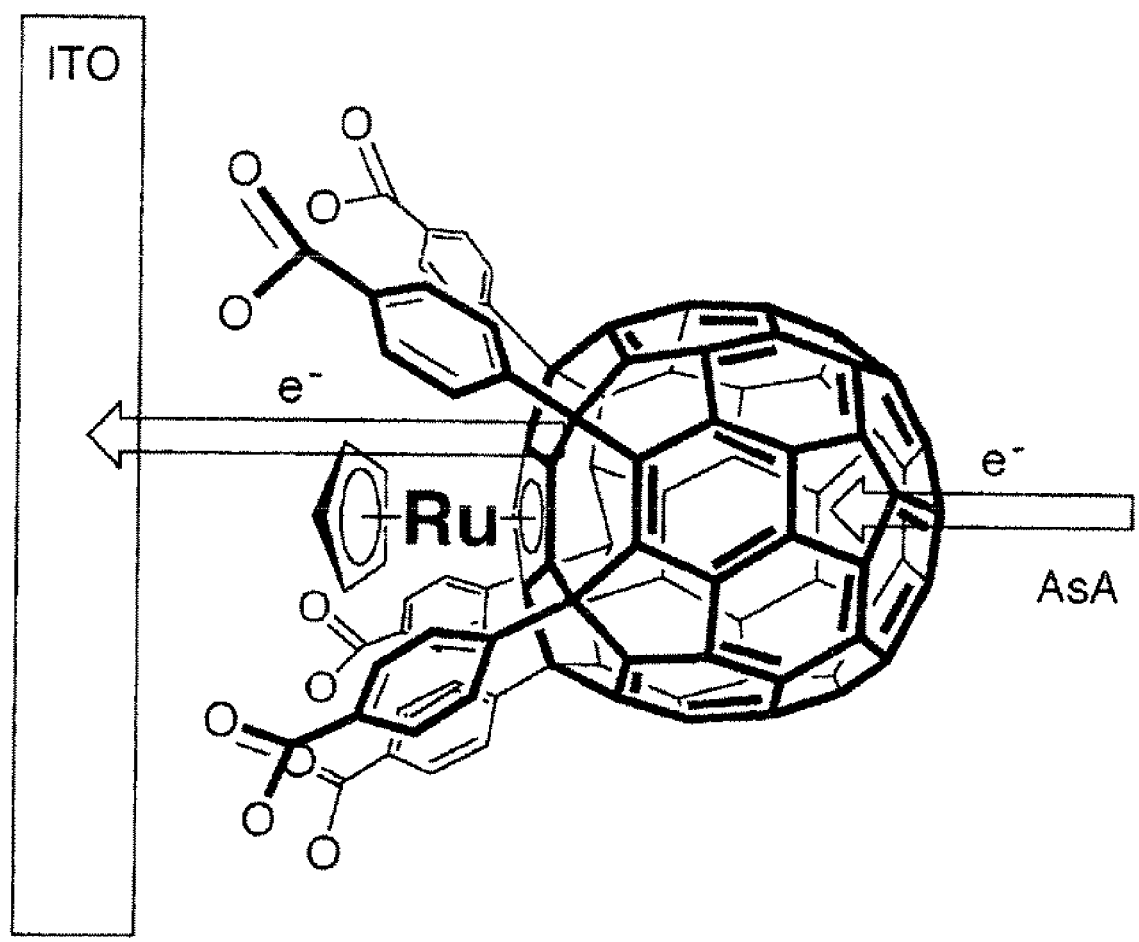
FIG. 2 shows a mechanism of photoelectric conversion using a photoelectric conversion device.

Using FIG. 1, one example of a photoelectric conversion device, wherein a monomolecular film of a fullerene derivative comprising a Fe atom is formed on an ITO electrode, and in which cathode current flows, will be explained. Initially, when optical energy (hv) irradiated from outside is absorbed by a bucky metallocene derivative comprising a Fe atom, the metallocene (Fe) site in the derivative provides electron to the fullerene site (FIG. 1-1) to cause the intramolecular charge-separated state (FIG. 1-2). After that, electron ($e^-$) entered into LUMO of the fullerene derivative is provided to an electrolyte solution constituting the charge transfer layer in which oxygen and methyl viologen ($MV^{2+}$) are dissolved, and at the same time, the ITO electrode provides electron ($e^-$) to the metallocene (Fe) site (FIG. 1-3). As a result, cathode current is generated, and current flows through a circuit connected to the solar cell.

Using FIG. 2, one example of a photoelectric conversion device, wherein a monomolecular film of a fullerene derivative comprising a Ru atom is formed on an ITO electrode, and in which anode current flows, will be explained. Initially, when optical energy (hv) irradiated from outside is absorbed by a bucky metallocene derivative comprising a Ru atom, ascorbic acid (ASA) constituting the charge transfer layer provides electron ($e^-$) to the fullerene, and electron ($e^-$) entered into LUMO of the fullerene derivative is provided to an ITO electrode. As a result, anode current is generated, and current flows through a circuit connected to the solar cell.

EXAMPLES

Hereinafter, the present invention will be more specifically described by way of examples. However, the present invention is not limited only to these examples.

Synthesis Example 1

Production of $C_{60}(C_6H_4COOEt-4)_5H$ 2.0 g of fullerene $C_{60}$ was dissolved in 90 mL of orthodichlorobenzene under nitrogen atmosphere. To the obtained mixture, 15 equivalents of ethoxycarbonylmethylzinc bromide reagent $BrZnCH_2CO_2Et$ in THF solution (concentration: about 0.7 M; as the halogenated organic compound (A)), 15 equivalents of copper (I) bromide-dimethylsulfide complex $CuBr.S(CH_3)_2$ (as the copper compound (B)), and 15 equivalents of N,N-dimethylimidazolidinone (4.75 g) were added, and reaction was performed at 25° C. 2.5 hours later, 2.0 mL of saturated ammonium chloride solution was added to the mixture to terminate the reaction. The reaction product was diluted by the addition of 10 mL of deaerated toluene, and the mixture was passed through a short-pass silica gel column using toluene as a developing solvent to remove by-products such as zinc salt, etc. The solvent was distilled away, and 100 mL of methanol was added. A solid obtained by reprecipitation was subjected to filtration, and thereafter it was washed with methanol to obtain 2.94 g of penta(organo)fullerene derivative $C_{60}(C_6H_2COOEt-4)_5H$ (isolated yield: 92%).

NMR analysis data of the obtained product are as follows:

$^1$H NMR (CDCl$_3$) δ 5.16 (s, 1H, CpH), 4.28 (q, J=7.16 Hz, 2 H), 4.25 (q, J=7.16 Hz, 4 H), 4.22 (q, J=7.16 Hz, 4 H), 3.71 (s, 2 H), 3.69 (d, J=14.3 Hz, 1 H), 3.61 (d, J=14.6 Hz, 1 H), 3.54 (d, J=14.6 Hz, 1 H), 3.50 (d, J=14.3 Hz, 1 H), 1.29 (t, J=7.16 Hz, 3 H), 1.28 (t, J=7.16 Hz, 6 H), 1.24 (t, J=7.16 Hz, 6 H).

$^{13}$C NMR (CDCl$_3$) δ 171.32, 170.49, 169.91, 155.17 (2C), 153.34 (2C), 152.15 (2C), 150.57 (2C), 148.59 (2C), 148.55 (2C), 148.24 (2C), 148.04 (2C), 148.00 (1C), 147.87 (2C), 147.63 (2C), 147.04 (2C), 146.92 (2C), 146.85 (1C), 146.52 (2C), 145.48 (2C), 145.13 (2C), 145.03 (2C), 144.56 (2C), 144.13 (2C), 144.01 (2C), 143.86 (2C), 143.85 (2C), 143.78 (2C), 143.69 (2C), 143.69 (2C), 143.57 (2C), 142.75 (2C), 61.23 (1C, CH$_2$CH$_3$), 61.18 (2C, CH$_2$CH$_3$), 61.14 (2C, CH$_2$CH$_3$), 57.56 (1C), 53.79 (2C), 52.39 (1C), 51.55 (2C), 44.58 (3C, CCO$_2$), 44.09 (2C, CO$_2$), 14.26 (2C CH$_3$CH$_3$), 14.22 (3C, CH$_2$CH$_3$).

Synthesis Example 2

Production of FeC$_{60}$(C$_6$H$_4$COOH-4)$_5$Cp $C_{60}(C_6H_4COOEt-4)_5H$ obtained in Synthesis Example 1 (292 mg, 0.200 mmol) was dissolved in benzonitrile (40 mL). [FeCP(CO)$_2$]$_2$ (355 mg, 1.00 mmol) was added thereto, and the mixture was heated and stirred at 180° C. for 48 hours. After cooled, the mixture was passed through a short-pass silica gel chromatography using toluene as a developing solvent to remove by-products such as metal salt, etc. The solvent was distilled away, and isolation was performed by means of flash column chromatography to obtain 176 mg of FeC$_{60}$(C$_6$H$_4$COOEt-4)$_5$Cp (isolated yield: 55.5%).

NMR, IR and APCI-MS analysis data of the obtained product are as follows:

$^1$H NMR (CDCl$_3$): δ1.47 (t, J=7.00 Hz, 15H, CH$_3$), 3.24 (s, 5H, Cp), 4.45 (q, J=6.85 Hz, 10H, CH$_2$), 7.95 (d, J=8.05 Hz, 10H, ArH), 8.04 (d, J=8.00 Hz, 10H, ArH). $^{13}$C NMR (CDCl$_3$): (14.36 (5C, CH$_3$), 58.24 (5C, C$_{60}$(sp$^3$)), 61.32 (5C, CH$_2$), 73.52 (5C, Cp), 92.12 (5C, C$_{60}$(C$_{Cp}$)), 128.82 (10C, Ar), 129.01 (5C, Ar), 129.41 (10C, Ar), 130.13 (5C, Ar), 143.16 (10C, C$_{60}$), 143.53 (10C, C$_{60}$), 147.25 (5C, C$_{60}$), 147.32 (5C, C$_{60}$), 147.98 (10C, C$_{60}$), 148.31 (5C, C$_{60}$), 151.75 (5C, C$_{60}$), 165.91 (5C, CO$_2$Et).

IR (powder, cm$^{-1}$): 2977 ($v_{C-H}$), 1713 (s, $v_{C=O}$), 1607 (s), 1268 (s), 1100 (s), 1019 (s), 752 (s), 696 (s).

APCI-MS (−): m/z 1586 (M$^-$). APCI-HRMS (−): calcd for C$_{110}$H$_{50}$FeO$_{10}$ (M$^-$) 1586.2753, found 1586.2792.

Next, the obtained FeC$_{60}$(C$_6$H$_4$COOEt-4)$_5$Cp (15.8 mg, 0.0100 mmol) was dissolved in toluene (5 mL). Sodium hydroxide in methanol solution (0.5 M, 0.20 mL, 0.10 mmol) was added thereto, and the mixture was stirred at 60° C. for 30 minutes. After cooled, the precipitate separated out was filtered and washed with hexane. The solid was treated with 1N hydrochloric acid (2 mL), washed with water and then dried to obtain 15.0 mg of FeC$_{60}$(C$_6$H$_4$COOH-4)$_5$Cp (solid) represented by the following formula (20) (yield: 95.0%).

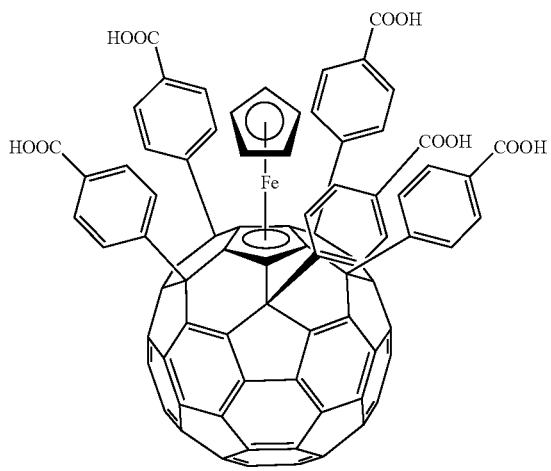

(20)

NMR, IR and APCI-MS analysis data of the obtained product are as follows:

$^1$H NMR (THF-d8): δ3.36 (s, 5H, Cp), 8.05 (d, J=8.40 Hz, 10H, ArH), 8.08 (d, J=8.40 Hz, 10H, ArH), 11.63 (s, 5H, COOH). $^{13}$C NMR (THF-d8): (59.55 (5C, C$_{60}$(sp$^3$)), 74.57 (5C, Cp), 93.41 (5C, C$_{60}$(C$_{Cp}$)), 130.02 (10C, Ar), 130.24 (10C, Ar), 130.46 (5C, Ar), 131.29 (5C, Ar), 144.19 (10C, C$_{60}$), 144.83 (10C, C$_{60}$), 148.26 (5C, C$_{60}$), 148.36 (5C, C$_{60}$), 149.16 (10C, C$_{60}$), 149.43 (5C, C$_{60}$), 153.25 (5C, C$_{60}$), 166.44 (5C, CO$_2$H).

IR (powder, cm$^{-1}$): 3222 (br, $v_{O-H}$), 2921 ($v_{C-H}$), 2850 (m), 1720 (s, $v_{C=O}$), 1607 (s), 1275 (s, $v_{C-O}$), 1208 (s).

APCI-MS (−): m/z 1446 (M$^-$). APCI-HRMS (−): calcd for C$_{100}$H$_{29}$FeO$_{10}$ (M$^-$−H) 1445.1110, found 1445.1101.

Synthesis Example 3

Production of RuC$_{60}$(C$_6$H$_4$COOH-4)$_5$Cp $C_{60}(C_6H_4COOEt-4)_5H$ obtained in Synthesis Example 1 (100 mg, 0.0682 mmol) was dissolved in THF (5 mL). 1.0 M t-BuOK in THF solution (0.0700 mL, 0.0700 mmol) and RuCp(CH$_3$CN)$_3$ (30.0 mg, 0.0691 mmol) were added thereto, and the mixture was stirred at room temperature for 1 hour. After that, the mixture was passed through a short-pass silica gel chromatography using toluene as a developing solvent to remove by-products such as metal salt, etc. The solvent was distilled away, and HPLC was used to obtain 13.0 mg of RuC$_{60}$(C$_6$H COOEt-4)$_5$Cp (isolated yield: 11.1%).

NMR and APCI-MS analysis data of the obtained product are as follows:

$^1$H NMR (CDCl$_3$): δ1.45 (t, J=7.45 Hz, 15H, CH$_3$), 3.64 (s, 5H, Cp), 4.44 (q, J=6.90 Hz, 10H, CH$_2$), 7.75 (d, J=8.00 Hz, 10H, ArH), 7.93 (d, J=8.60 Hz, 10H, ArH). $^{13}$C NMR (CDCl$_3$): (14.37 (5C, CH$_3$), 58.04 (5C, C$_{60}$(sp$^3$)), 61.38 (5C, CH$_2$), 77.86 (5C, Cp), 98.93 (5C, C$_{60}$(C$_{Cp}$)), 128.19 (10C, Ar), 128.55 (5C, Ar), 129.07 (10C, Ar), 130.03 (5C, Ar), 143.44 (10C, C$_{60}$), 143.91 (10C, C$_{60}$), 147.46 (5C, C$_{60}$), 148.06 (5C, C$_{60}$), 148.25 (10C, C$_{60}$), 148.65 (5C, C$_{60}$), 151.80 (5C, C$_{60}$), 166.05 (5C, CO$_2$Et).

APCI-MS (−): m/z 1632 (M−)

APCI-HRMS (−): calcd for C100H50RuO$_{10}$ (M−H+) 1632.2447, found 1632.2420.

The obtained RuC$_{60}$(C$_6$H$_4$COOEt-4)$_5$Cp (22.8 mg, 0.0140 mmol) was dissolved in toluene (7 mL). To the mixture, sodium hydroxide in methanol solution (0.5 M, 0.28 mL, 0.14 mmol) was added, and the mixture was stirred at 60° C. for 30 minutes. After cooled, the precipitate separated out was filtered and washed with hexane. The solid was treated with 1N hydrochloric acid (2 mL), washed with water and dried to obtain 17.0 mg of $RuC_{60}(C_6H\ COOH\text{-}4)_5Cp$ (solid) represented by the following formula (21) (yield: 81.6%).

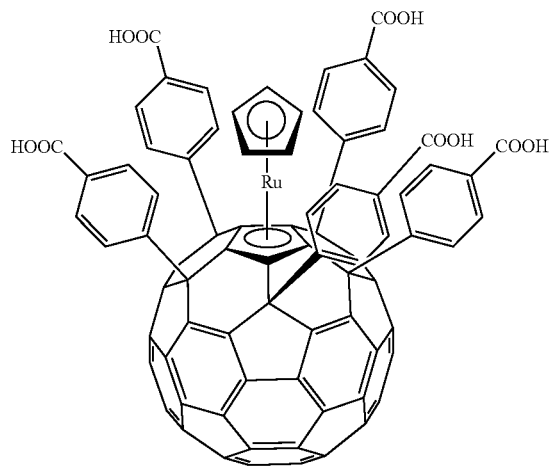

(21)

NMR and APCI-MS analysis data of the obtained product are as follows:

$^1$H NMR (THF-d8): δ3.77 (s, 5H, Cp), 7.84 (d, J=8.60 Hz, 10H, ArH), 7.98 (d, J=8.00 Hz, 10H, ArH), 11.56 (s, 5H, COOH). $^{13}$C NMR (THF-d8): (59.36 (5C, $C_{60}(sp^3)$), 78.85 (5C, Cp), 100.10 (5C, $C_{60}(C_{Cp})$), 128.87 (10C, Ar), 129.57 (10C, Ar), 129.64 (5C, Ar), 130.09 (5C, Ar), 131.71 (10C, $C_{60}$), 144.25 (10C, $C_{60}$), 145.10 (5C, $C_{60}$), 148.41 (5C, $C_{60}$), 149.16 (10C, $C_{60}$), 149.48 (5C, $C_{60}$), 153.27 (5C, $C_{60}$), 167.01 (5C, $CO_2H$).

APCI-MS (−): m/z 1491 (M−)

APCI-HRMS (−): calcd for $C_{100}H_{29}RuO_{10}$ (M−H+) 1491.0895, found 1491.0889.

Synthesis Example 4

Production of $FeC_{60}(BiPhCOOH\text{-}4)_5Cp$ $C_{60}(BiPhCOOEt\text{-}4)_5H$ (292 mg, 0.200 mmol) was dissolved in benzonitrile (40 mL). $[FeCp(CO)_2]_2$ (355 mg, 1.00 mmol) was added thereto, and the mixture was heated and stirred at 180° C. for 48 hours. After cooled, the mixture was passed through a short-pass silica gel chromatography using toluene as a developing solvent to remove by-products such as metal salt, etc. The solvent was distilled away, and flash column chromatography was applied to obtain 176 mg of $FeC_{60}(BiPhCOOEt\text{-}4)_5Cp$ (isolated yield: 55.5%).

NMR and APCI-MS analysis data of the obtained product are as follows:

$^1$H NMR (CDCl$_3$): δ1.47 (t, J=7.00 Hz, 15H, CH$_3$), 3.24 (s, 5H, Cp), 4.45 (q, J=6.85 Hz, 10H, CH$_2$), 7.95 (d, J=8.05 Hz, 10H, ArH), 8.04 (d, J=8.00 Hz, 10H, ArH). $^{13}$C NMR (CDCl$_3$): (14.36 (5C, CH$_3$), 58.24 (5C, $C_{60}(sp^3)$), 61.32 (5C, CH$_2$), 73.52 (5C, Cp), 92.12 (5C, $C_{60}(C_{Cp})$), 128.82 (10C, Ar), 129.01 (5C, Ar), 129.41 (10C, Ar), 130.13 (5C, Ar), 143.16 (10C, $C_{60}$), 143.53 (10C, $C_{60}$), 147.25 (5C, $C_{60}$), 147.32 (5C, $C_{60}$), 147.98 (10C, $C_{60}$), 148.31 (5C, $C_{60}$), 151.75 (5C, $C_{60}$), 165.91 (5C, $CO_2Et$).

APCI-MS (−): m/z 1966 (M−), 1845 (M-FeCp). APCI-HRMS (−): calcd for $C_{140}H_{70}FeO_{10}$(M−) 1966.4318, found 1966.4281.

The obtained $FeC_{60}(BiPhCOOEt\text{-}4)_5Cp$ (15.8 mg, 0.0100 mmol) was dissolved in toluene (5 mL). After that, sodium hydroxide in methanol solution (0.5 M, 0.20 mL, 0.10 mmol) was added thereto, and the mixture was stirred at 60° C. for 30 minutes. After cooled, the precipitate separated out was filtered and washed with hexane. The solid was treated with 1N hydrochloric acid (2 mL), washed with water and then dried to obtain 15.0 mg of $FeC_{60}(BiPhCOOH\text{-}4)_5Cp$ (solid) represented by the following formula (22) (yield: 95.0%).

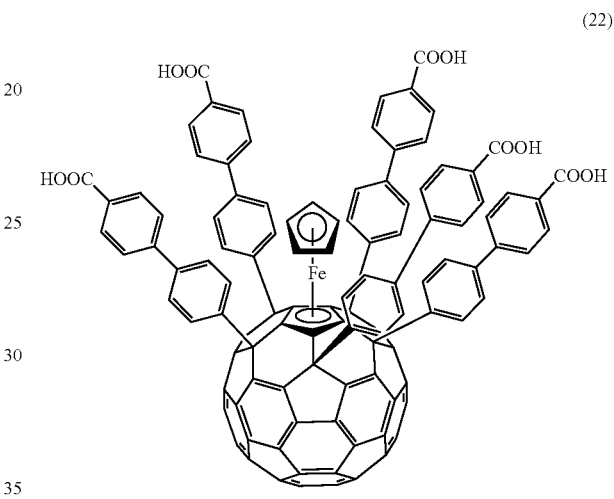

(22)

NMR and APCI-MS analysis data of the obtained product are as follows:

$^1$H NMR (THF-d8): δ3.36 (s, 5H, Cp), 8.05 (d, J=8.40 Hz, 10H, ArH), 8.08 (d, J=8.40 Hz, 10H, ArH), 11.63 (s, 5H, COOH). $^{13}$C NMR (THF-d8): (59.55 (5C, $C_{60}(sp^3)$), 74.57 (5C, Cp), 93.41 (5C, $C_{60}(C_{Cp})$), 130.02 (10C, Ar), 130.24 (10C, Ar), 130.46 (5C, Ar), 131.29 (5C, Ar), 144.19 (10C, $C_{60}$), 144.83 (10C, $C_{60}$), 148.26 (5C, $C_{60}$), 148.36 (5C, $C_{60}$), 149.16 (10C, $C_{60}$), 149.43 (5C, $C_{60}$), 153.25 (5C, $C_{60}$), 166.44 (5C, $CO_2H$).

APCI-MS (−): m/z 1826 (M−).

Synthesis Example 5

Production of $RuC_{60}(BiPhCOOH\text{-}4)_5Cp$ $C_{60}(BiPhCOOEt\text{-}4)_5H$ (146 mg, 0.0789 mmol) was dissolved in THF (7 mL). 1.0 M t-BuOK in THF solution (0.0813 mL, 0.0813 mmol) and $RuCp(CH_3CN)_3$ (34.6 mg, 0.0796 mmol) were added thereto, and the mixture was stirred at room temperature for 1 hour. After that, the mixture was passed through a short-pass silica gel chromatography using toluene as a developing solvent to remove by-products such as metal salt, etc. The solvent was distilled away, and HPLC was used to obtain 51.8 mg of $RuC_{60}(BiPhCOOEt\text{-}4)_5Cp$ (isolated yield: 33%).

NMR and APCI-MS analysis data of the obtained product are as follows:

$^1$H NMR (CDCl$_3$): δ1.33 (t, J=6.88 Hz, 15H, CH$_3$), 3.69 (s, 5H, Cp), 4.32 (q, J=6.88 Hz, 10H, CH$_2$), 7.45 (d, J=8.24 Hz, 10H, Ar), 7.60 (d, J=8.24 Hz, 10H, Ar), 7.77 (d, J=8.24 Hz,

10H, Ar), 8.30 (d, J=8.24 Hz, 10H, Ar). $^{13}$C NMR (CDCl$_3$): (14.32 (5C, CH$_3$), 58.05 (5C, C$_{60}$(sp$^3$)), 61.05 (5C, CH$_2$), 77.54 (5C, Cp), 99.46 (5C, C$_{60}$(C$_{Cp}$)), 126.39, 126.91, 129.43, 129.59, 130.14, 139.40, 143.40, 143.68, 144.12, 144.26, 147.40, 166.31 (5C, CO$_2$Et).

APCI-HRMS (−): calcd for C140H70RuO10(M−) 2012.40124, found 2012.40985.

The obtained RuC$_{60}$(BiPhCOOEt-4)$_5$Cp (47.2 mg, 0.024 mmol) was dissolved in toluene (10 mL). Sodium hydroxide in methanol solution (0.5 M, 0.47 mL, 0.24 mmol) was added thereto, and the mixture was stirred at 60° C. for 1 hour. After cooled, the precipitate separated out was filtered and washed with hexane. The solid was treated with 1N hydrochloric acid (3 mL), washed with water and then dried to obtain 35.3 mg of RuC$_{60}$(BiPhCOOH-4)$_5$Cp (solid) represented by the following formula (23) (yield: 81%).

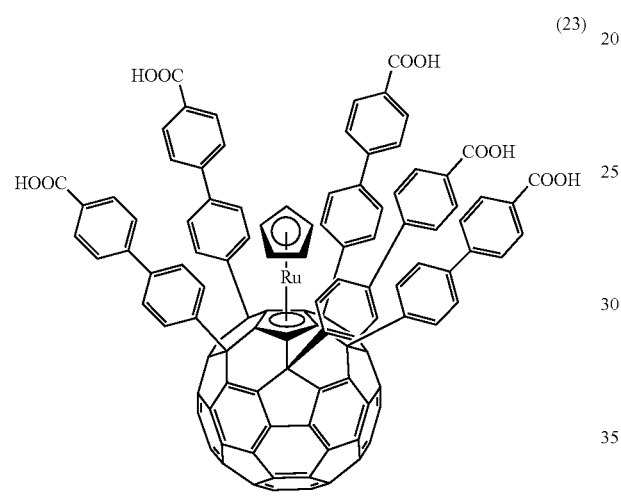

(23)

NMR and APCI-MS analysis data of the obtained product are as follows:

$^1$H NMR (THF-d8): δ3.95 (s, 5H, Cp), 7.72 (d, J=8.24 Hz, 10H, ArH), 7.81 (d, J=8.24 Hz, 10H, ArH), 7.95 (d, J=8.24 Hz, 10H, ArH). $^{13}$C NMR (THF-d8): (59.21 (5C, C$_{60}$(sp$^3$)), 78.52 (5C, Cp), 100.30, 127.23, 127.55, 130.28, 130.63, 130.90, 140.36, 144.15, 144.29, 144.76, 145.21, 148.33, 149.07, 149.34, 153.62, 167.28 (5C, CO$_2$H).

APCI-HRMS(−): calcd for C140H50RuO10 (M-H+) 1872.2247, found 1872.2492.

Synthesis Example 6

Production of C$_{60}$(CH$_3$)$_5$C$_3$H$_6$Si(OCH$_3$)$_3$

As shown in the below Scheme 3, under nitrogen atmosphere, 106 mg of C$_{60}$(CH$_3$)$_5$H was dissolved in 5 mL of THF. 1 equivalent of t-BuOK in THF solution was added thereto, then 2 equivalents of 3-trimethoxysilylpropyl chloride was added thereto, and the mixture was reacted at 45° C. for 24 hours. After that, the reaction mixture was cooled to room temperature, and 0.2 mL of aqueous solution of ammonium chloride was added thereto to quench the reaction. 300 mL of methanol was added to the mixture, and a solid obtained by reprecipitation was filtered. After that, the solid was washed with methanol to obtain 128 mg of C$_{60}$(CH$_3$)$_5$C$_3$H$_6$Si(OCH$_3$)$_3$ (isolated yield: 88%).

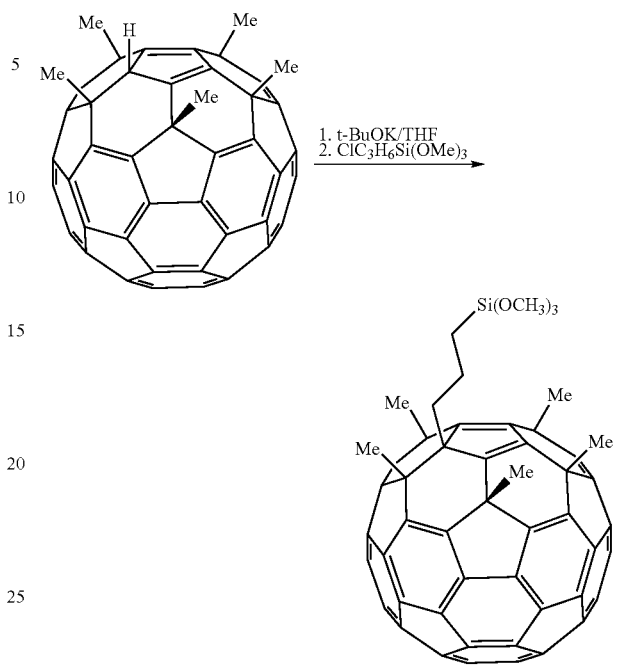

Scheme 3

NMR and APCI-MS analysis data of the obtained product are as follows:

$^1$H NMR (500 MHz, CDCl$_3$): δ 0.90 (t, J=8.0 Hz, 2H, SiCH$_2$), 2.00 (m, 2H, SiCH$_2$CH$_2$), 2.21 (s, 6H, C$_{60}$CH$_3$), 2.33 (s, 6H, C$_{60}$CH$_3$), 2.40 (s, 3H, C$_{60}$CH$_3$), 2.60 (t, J=8.0 Hz, 2H, C$_{60}$CH$_2$), 3.71 (s, 9H, OCH$_3$). APCI-HRMS (−): calcd for C$_{71}$H$_{28}$O$_3$Si (M$^-$-H) 958.1964, found 958.2002.

Example 1

Photoelectric Conversion Device Comprising the Fullerene Derivative Obtained in Synthesis Example 2

An ITO electrode, wherein ITO was deposited on the surface of a transparent glass slide to get 10 Ω/sq, was immersed in 0.1 mM THF solution of the fullerene derivative FeC$_{60}$ (C$_6$H$_4$COOH-4)$_5$Cp obtained in Synthesis Example 2 at 23° C. for 72 hours to prepare a self-assembled monomolecular film on ITO, and thereby a photoelectric conversion device was obtained.

Anode current of the ferrocene portion of the photoelectric conversion device was measured using a cyclic voltammetry method, and the amount of the current was integrated. As a result, the amount of faradaic current (S) was 9.7 μCcm$^{-2}$. According to the below formula, the amount of adsorption per ITO unit area, i.e., the number of molecules immobilized on the electrode (Γ) was 0.1 nmolcm$^{-2}$.

Γ=S/F (F=Faraday constant: 96500 Cmol$^{-1}$)
Γ=9.7 μCcm$^{-2}$/96500 Cmol$^{-1}$=0.1 nmolcm$^{-2}$ Example 2

Photoelectric Conversion Device Comprising the Fullerene Derivative Obtained in Synthesis Example 3

A self-assembled monomolecular film was prepared on ITO in a manner similar to that in Example 1 except that the fullerene derivative $RuC_{60}(C_6H_4COOH-4)_5Cp$ obtained in Synthesis Example 3 was used, and a photoelectric conversion device was produced. Further, when the number of molecules immobilized on the electrode (Γ) was measured in a manner similar to that in Example 1, it was 0.1 nmolcm$^{-2}$.

Example 3

Photoelectric Conversion Device Comprising the Fullerene Derivative Obtained in Synthesis Example 4

A self-assembled monomolecular film was prepared on ITO in a manner similar to that in Example 1 except that the fullerene derivative $FeC_{60}(BiPhCOOH-4)_5Cp$ obtained in Synthesis Example 4 was used, and a photoelectric conversion device was produced. Further, when the number of molecules immobilized on the electrode (Γ) was measured in a manner similar to that in Example 1, it was 0.08 nmolcm$^{-1}$.

Example 4

Photoelectric Conversion Device Comprising the Fullerene Derivative Obtained in Synthesis Example 5

A self-assembled monomolecular film was prepared on ITO in a manner similar to that in Example 1 except that the fullerene derivative $RuC_{60}(BiPhCOOH-4)_5Cp$ obtained in Synthesis Example 5 was used, and a photoelectric conversion device was produced. Further, when the number of molecules immobilized on the electrode (Γ) was measured in a manner similar to that in Example 1, it was 0.08 nmolcm$^{-2}$.

Comparative Example 1

Photoelectric Conversion Device Comprising the Fullerene Derivative Obtained in Synthesis Example 6

A self-assembled monomolecular film was prepared on ITO in a manner similar to that in Example 1 except that the fullerene derivative $C_{60}(CH_3)_5C_3H_6Si(OCH_3)_3$ obtained in Synthesis Example 6 was used, and a photoelectric conversion device was produced. Further, when the number of molecules immobilized on the electrode (Γ) was measured in a manner similar to that in Example 1, it was 0.24 nmolcm$^{-2}$.

Example 5

Solar Cell Comprising the Photoelectric Conversion Device in Example 1

The photoelectric conversion device laminated with the self-assembled monomolecular film of $FeC_{60}(C_6H_4COOH-4)_5Cp$ obtained in Example 1 was used as a work electrode, and a platinum wire was used as a counter electrode. These two electrodes were positioned to be opposed in an electrolyte solution, wherein oxygen ($O_2$) and methyl viologen ($MV^{2+}$) (as electron acceptors) were dissolved in an aqueous solution comprising 0.1 mol of sodium sulfate, and thereby the solar cell of the present invention was produced. In this case, the electrolyte solution exists between the two electrodes to function as a charge transfer layer.

Further, using an Ag/AgCl electrode as a reference electrode, under the condition of temperature at 25° C., the aforementioned solar cell was subjected to photocurrent measurement.

When the electrical potential of the work electrode was set as 0 V and the solar cell was irradiated with monochromatic light from a Xe lamp (wavelength: 400 nm, intensity: 407 µW), cathode current was observed. In this case, the absorbance (A) was $2.34 \times 10^{-4}$, and the photocurrent (i) was $11.3 \times 10^{-9}$A.

According to the below formula, the quantum yield (φ), which represents the ratio of the number of electrons flowed to the number of photons absorbed by the compound on ITO, was 16%.

Quantum yield(φ)=$(i/e)/[I(1-10^{-A})] \times 100$(%)

In this regard, I=(Wλ/hc), which means the number of photons per unit time and unit area ($8.2 \times 10^{14}$WJ); i represents a photocurrent (A); and A represents absorbance at λ nm. Further, e represents elementary charge (C)=$1.60 \times 10^{-19}$C; W represents light irradiation power (W) at λ nm=$407 \times 10^{-6}$W (used in the experiment); λ represents wavelength of light irradiation (m)=400 nm (used in the experiment); h represents Planck's constant (Js)=$6.63 \times 10^{-34}$Js; and c represents light speed (ms$^{-1}$)=$3.00 \times 10^8$ ms$^{-1}$.

When the electrical potential of the work electrode was set as −0.12 V and bias voltage was provided, the photocurrent (i) was $24.0 \times 10^{-9}$A. In this case, the quantum yield (φ) was 24%.

Further, the photocurrent spectrum obtained when irradiated with light having the wavelength of 400 to 600 nm showed almost the same shape as the absorption spectrum of $FeC_{60}(C_6H_4COOH-4)_5Cp$ in THF solution. According to the result, it was confirmed that $FeC_{60}(C_6H_4COOH-4)_5Cp$ is the active center of photoelectric conversion.

Example 6

Solar Cell Comprising the Photoelectric Conversion Device in Example 2

The photoelectric conversion device laminated with the self-assembled monomolecular film of $RuC_{60}(C_6H_4COOH-4)_5Cp$ obtained in Example 2 was used as a work electrode, and a platinum wire was used as a counter electrode. These two electrodes were positioned to be opposed in an electrolyte solution, wherein ascorbic acid (AsA, as an electron donor) was dissolved in an aqueous solution comprising 0.1 mol of sodium sulfate, and thereby the solar cell of the present invention was produced. In this case, the electrolyte solution exists between the two electrodes to function as a charge transfer layer.

Further, using an Ag/AgCl electrode as a reference electrode, under the condition of temperature at 25° C., the aforementioned solar cell was subjected to photocurrent measurement.

When the electrical potential of the work electrode was set as 0 V and the solar cell was irradiated with monochromatic light from a Xe lamp (wavelength: 400 nm, intensity: 407 µW), anode current was observed. In this case, the absorbance (A) was $2.90 \times 10^{-4}$, and the photocurrent (i) was $44.0 \times 10^{-9}$A. According to the above formula, the quantum yield (φ), which represents the ratio of the number of electrons flowed to the number of photons absorbed by the compound on ITO, was 50%.

When the electrical potential of the work electrode was set as 0.1 V and bias voltage was provided, the photocurrent (i) was $88.0 \times 10^{-9}$A. In this case, the quantum yield (φ) was 100%.

Example 7

Solar Cell Comprising the Photoelectric Conversion Device in Example 3

The solar cell of the present invention was produced in a manner similar to that in Example 5 except that the photoelectric conversion device in Example 3 was used.

When the electrical potential of the work electrode was set as 0 V and the solar cell was irradiated with monochromatic light from a Xe lamp (wavelength: 400 nm, intensity: 407 μW) in a manner similar to that in Example 5, cathode current was observed. In this case, the absorbance (A) was $1.9 \times 10^{-4}$, and the photocurrent (i) was $12.0 \times 10^{-9}$ A. According to the above-described formula, the quantum yield ($\phi$), which represents the ratio of the number of electrons flowed to the number of photons absorbed by the compound on ITO, was 21%.

When the electrical potential of the work electrode was set as −0.12 V and bias voltage was provided, the photocurrent (i) was $21.2 \times 10^{-9}$ A. In this case, the quantum yield ($\phi$) was 37%.

Example 8

Solar Cell Comprising the Photoelectric Conversion Device in Example 4

The solar cell of the present invention was produced in a manner similar to that in Example 6 except that the photoelectric conversion device in Example 4 was used.

When the electrical potential of the work electrode was set as 0 V and the solar cell was irradiated with monochromatic light from a Xe lamp (wavelength: 400 nm, intensity: 407 μW) in a manner similar to that in Example 6, anode current was observed. In this case, the absorbance (A) was $1.87 \times 10^{-4}$, and the photocurrent (i) was $28.0 \times 10^{-9}$ A. According to the above-described formula, the quantum yield ($\phi$), which represents the ratio of the number of electrons flowed to the number of photons absorbed by the compound on ITO, was 50%.

When the electrical potential of the work electrode was set as 0.1 V and bias voltage was provided, the photocurrent (i) was $47.0 \times 10^{-9}$ A. In this case, the quantum yield ($\phi$) was 83%.

Example 9

Solar Cell Comprising the Photoelectric Conversion Device in Example 4

The solar cell of the present invention was produced in a manner similar to that in Example 5 except that the photoelectric conversion device in Example 4 was used.

When the electrical potential of the work electrode was set as 0 V and the solar cell was irradiated with monochromatic light from a Xe lamp (wavelength: 400 nm, intensity: 407 μW) in a manner similar to that in Example 5, cathode current was observed. In this case, the absorbance (A) was $1.87 \times 10^{-4}$, and the photocurrent (i) was $19.0 \times 10^{-9}$ A. According to the above-described formula, the quantum yield ($\phi$), which represents the ratio of the number of electrons flowed to the number of photons absorbed by the compound on ITO, was 34%.

When the electrical potential of the work electrode was set as −0.15 V and bias voltage was provided, the photocurrent (i) was $32.3 \times 10^{-9}$ A. In this case, the quantum yield ($\phi$) was 57%.

Comparative Example 2

Solar Cell Comprising the Photoelectric Conversion Device in Comparative Example 1

A solar cell was produced in a manner similar to that in Example 6 except that the photoelectric conversion device in Comparative Example 1 was used.

When the electrical potential of the work electrode was set as 0 V and the solar cell was irradiated with monochromatic light from a Xe lamp (wavelength: 400 nm, intensity: 407 μW) in a manner similar to that in Example 6, anode current was observed. In this case, the absorbance (A) was $5.18 \times 10^{-4}$, and the photocurrent (i) was $4.4 \times 10^{-9}$ A. According to the above-described formula, the quantum yield ($\phi$), which represents the ratio of the number of electrons flowed to the number of photons absorbed by the compound on ITO, was 2.8%.

When the electrical potential of the work electrode was set as 0.07 V and bias voltage was provided, the photocurrent (i) was $12.8 \times 10^{-9}$ A. In this case, the quantum yield ($\phi$) was 8.2%.

Further, the photocurrent spectrum obtained when irradiated with light having the wavelength of 400 to 600 nm showed almost the same shape as the absorption spectrum of $C_{60}(CH_3)_5C_3H_6Si(OCH_3)_3$ in THF solution. According to the result, it was confirmed that $C_{60}(CH_3)_5C_3H_6Si(OCH_3)_3$ is the active center of photoelectric conversion.

Industrial Applicability

The photoelectric conversion material and the photoelectric conversion device obtained in the present invention can be utilized, for example, for organic solar cell, etc.

The invention claimed is:

1. A photoelectric conversion device having a self-assembled monomolecular film of a photoelectric conversion material comprising a fullerene derivative represented by the following formula (1):

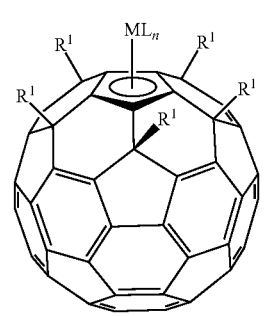

(1)

wherein: each $R^1$ independently represents an organic group having a substituent; M represents a metal atom; L is a ligand of M; and n is the number of Ls.

2. A solar cell having the photoelectric conversion device according to claim 1.

3. A photoelectric conversion material comprising a fullerene derivative represented by the following formula (11):

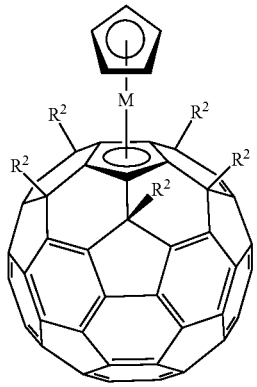

(11)

wherein:

each $R^2$ is independently a group represented by the following formula (A):

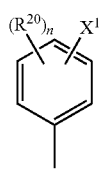

(A)

wherein: $X^1$ represents a carboxylic acid group, a phosphate group or a phosphonate group; each $R^{20}$ independently represents an organic group; and n is an integer from 0 to 4; and M represents a metal atom.

4. A photoelectric conversion material comprising a fullerene derivative represented by the following formula (12):

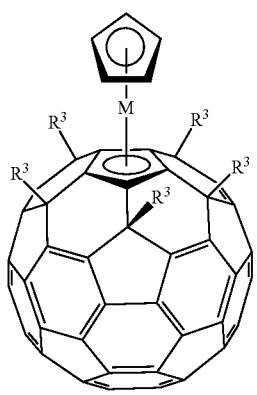

(12)

wherein:

each $R^3$ is independently a group represented by the following formula (B):

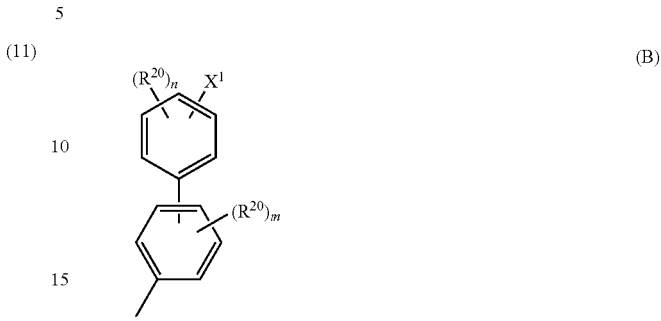

(B)

wherein: $X^1$ represents a carboxylic acid group, a phosphate group, a phosphonate group; each $R^{20}$ independently represents an organic group; n is an integer from 0 to 4; and m is an integer from 0 to 4; and M represents a metal atom.

5. A photoelectric conversion device having a self-assembled monomolecular film of a photoelectric conversion material comprising a fullerene derivative represented by the following formula (10):

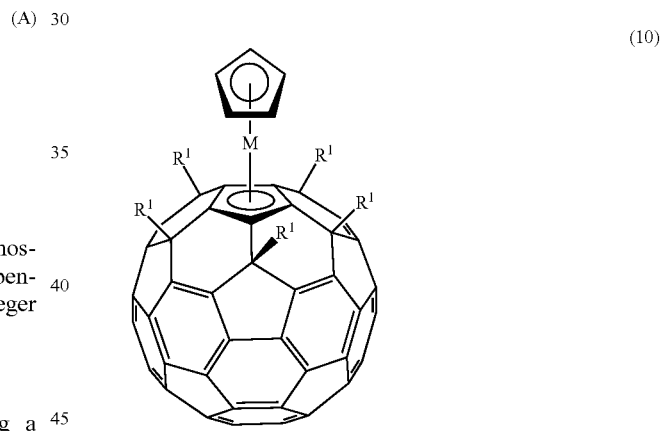

(10)

wherein: each $R^1$ independently represents a $C_1$-$C_{30}$ hydrocarbon group, a $C_1$-$C_{30}$ alkoxy group, a $C_6$-$C_{30}$ aryloxy group, an amino group, a silyl group, an alkylthio group (—$SY^1$: in the formula, $Y^1$ represents a substituted or unsubstituted group $C_1$-$C_{30}$ alkyl group), an arylthio group (—$SY^2$: in the formula, $Y^2$ represents a substituted or unsubstituted $C_6$-$C_{18}$ aryl group), an alkylsulfonyl group (—$SO_2Y^3$: in the formula, $Y^3$ represents a substituted or unsubstituted $C_1C_{30}$ alkyl group), or an arylsulfonyl group (—$SO_2Y^4$: in the formula, $Y^4$ represents a substituted or unsubstituted $C_6$-$C_{18}$ aryl group), which has a carboxylic acid group, a phosphate group, or a phosphonate group; and M represents a metal atom.

6. A photoelectric conversion device having an ITO electrode on which the self-assembled monomolecular film of a photoelectric conversion material is formed and wherein the photoelectric conversion material comprises a fullerene derivative represented by the following formula (10):

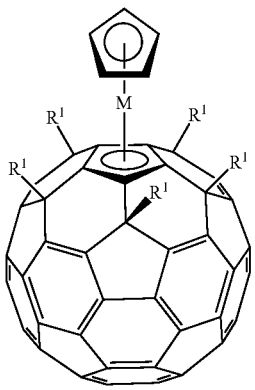

(10)

wherein: each $R^1$ independently represents a $C_1$-$C_{30}$ hydrocarbon group; a $C_1$-$C_{30}$ alkoxy group, a $C_6$-$C_{30}$ aryloxy group, an amino group, a silyl group, an alkylthio group (—$SY^1$: in the formula, $Y^1$ represents a substituted or unsubstituted $C_1$-$C_{30}$ alkyl group), an arylthio group (—$SY^2$: in the formula, $Y^2$ represents a substituted or unsubstituted $C_6$-$C_{18}$ aryl group), an alkylsulfonyl group (—$SO_2Y^3$: in the formula, $Y^3$ represents a substituted or unsubstituted $C_1$-$C_{30}$ alkyl group), or an arylsulfonyl group (—$SO_2Y^4$: in the formula, $Y^4$ represents a substituted or unsubstituted $C_6$-$C_{18}$ aryl group), which has a carboxylic acid group, a phosphate group, or a phosphonate group; and M represents a metal atom.

7. A solar cell having the photoelectric conversion device according to claim 5 or 6.

8. A photoelectric conversion device having a self-assembled monomolecular film of a photoelectric conversion material comprising a fullerene derivative represented by the following formula (10):

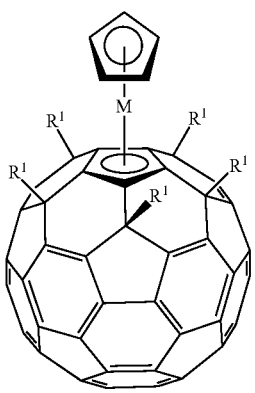

(10)

wherein: each $R^1$ independently represents a $C_1$-$C_{30}$ hydrocarbon group, a $C_1$-$C_{30}$ alkoxy group, a $C_6$-$C_{30}$ aryloxy group, an amino group, a silyl group, an alkylthio group (—$SY^1$: in the formula, $Y^1$ represents a substituted or unsubstituted $C_1$-$C_{30}$ alkyl group), an arylthio group (—$SY^2$: in the formula, $Y^2$ represents a substituted or unsubstituted $C_6$-$C_{18}$ aryl group), an alkylsulfonyl group (—$SO_2Y^3$: in the formula, $Y^3$ represents a substituted or unsubstituted $C_1$-$C_{30}$ alkyl group), or an arylsulfonyl group (—$SO_2Y^4$: in the formula, $Y^4$ represents a substituted or unsubstituted $C_6$-$C_{18}$ aryl group), which has a thiol group or a disulfide group; and M represents a metal atom.

9. A photoelectric conversion device having a gold electrode on which a self-assembled monomolecular film of a photoelectric conversion material is formed and wherein the photoelectric conversion material comprises a fullerene derivative represented by the following formula (10):

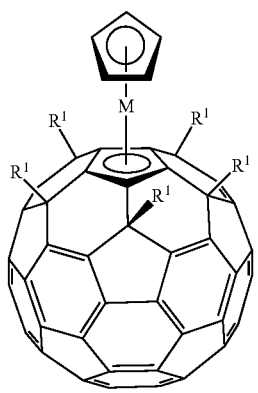

(10)

wherein: each $R^1$ independently represents a $C_1$-$C_{30}$ hydrocarbon group, a $C_1$-$C_{30}$ alkoxy group, a $C_6$-$C_{30}$ aryloxy group, an amino group, a silyl group, an alkylthio group (—$SY^1$: in the formula, $Y^1$ represents a substituted or unsubstituted $C_1$-$C_{30}$ alkyl group), an arylthio group (—$SY^2$: in the formula, $Y^2$ represents a substituted or unsubstituted $C_6$-$C_{18}$ aryl group), an alkylsulfonyl group (—$SO_2Y^3$: in the formula, $Y^3$ represents a substituted or unsubstituted $C_1$-$C_{30}$ alkyl group), or an arylsulfonyl group (—$SO_2Y^4$: in the formula, $Y^4$ represents a substituted or unsubstituted $C_6$-$C_{18}$ aryl group), which has a thiol group or a disulfide group; and M represents a metal atom.

10. A solar cell having the photoelectric conversion device according to claim 8.

11. A photoelectric conversion device having a self-assembled monomolecular film of a photoelectric conversion material comprising a fullerene derivative represented by the following formula (10):

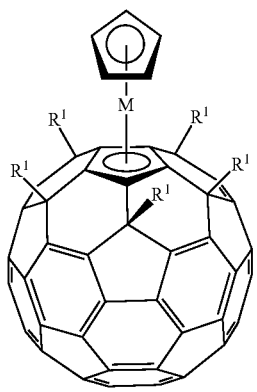

(10)

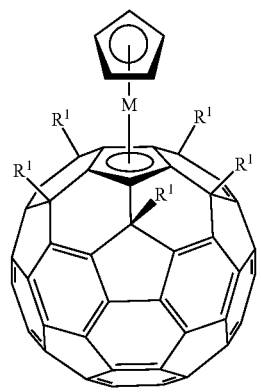

(10)

wherein: each $R^1$ independently represents a $C_1$-$C_{30}$ alkyl group, a $C_2$-$C_{30}$ alkenyl group, a $C_2$-$C_{30}$ alkynyl group, a $C_4$-$C_{30}$ alkyldienyl group, $C_6$-$C_{18}$ aryl group, a $C_7$-$C_{30}$ arylalkyl group, a $C_7$-$C_{30}$ cycloalkyl group, or a $C_4$-$C_{30}$ cycloalkenyl group, which has a thiol group or a disulfide group; and M represents a metal atom.

12. A photoelectric conversion device having a gold electrode on which a self-assembled monomolecular film of a photoelectric conversion material is formed and wherein the photoelectric conversion material comprises a fullerene derivative represented by the following formula (10):

wherein: each $R^1$ independently represents a $C_1$-$C_{30}$ alkly group, a $C_2$-$C_{30}$ alkenyl group, a $C_2$-$C_{30}$ alkynyl group, a $C_4$-$C_{30}$ alkyldienyl group, a $C_6$-$C_{18}$ aryl group, a $C_7$-$C_{30}$ alkylaryl group, a $C_7$-$C_{30}$ arylalkyl group, a $C_4$-$C_{30}$ cycloalkyl group or a $C_4$-$C_{30}$ cycloalkenyl group, which has a thiol group or a disulfide group; and M represents a metal atom.

13. A solar cell having the photoelectric conversion device according to claim 9.

\* \* \* \* \*